US010980786B2

(12) United States Patent
Cooper et al.

(10) Patent No.: US 10,980,786 B2
(45) Date of Patent: *Apr. 20, 2021

(54) MATERNAL VITAMIN B6 ADMINISTRATION FOR THE PREVENTION OF INCREASED ADIPOSITY, OVERWEIGHT OR OBESITY IN THE OFFSPRING

(71) Applicant: NESTEC S.A., Vevey (CH)

(72) Inventors: Cyrus Cooper, Southampton Hampshire (GB); Peter David Gluckman, Auckland (NZ); Keith Malcolm Godfrey, Ashurst Hampshire (GB); Catherine Mace, Lausanne (CH); Irma Silva Zolezzi, Carrouge (CH)

(73) Assignee: NESTEC S.A., Vevey (CH)

( * ) Notice: Subject to any disclaimer, the term of this patent is extended or adjusted under 35 U.S.C. 154(b) by 39 days.

This patent is subject to a terminal disclaimer.

(21) Appl. No.: 15/879,660

(22) Filed: Jan. 25, 2018

(65) Prior Publication Data

US 2018/0280369 A1    Oct. 4, 2018

Related U.S. Application Data

(63) Continuation of application No. 15/109,713, filed as application No. PCT/EP2015/050358 on Jan. 9, 2015, now Pat. No. 9,980,950.

(30) Foreign Application Priority Data

Jan. 10, 2014 (EP) .................................... 14150798
Mar. 21, 2014 (EP) .................................... 14161188

(51) Int. Cl.
*A61K 31/4415*  (2006.01)
*A23L 33/15*  (2016.01)
*A23L 33/00*  (2016.01)

(52) U.S. Cl.
CPC .......... *A61K 31/4415* (2013.01); *A23L 33/15* (2016.08); *A23L 33/30* (2016.08); *A23L 33/40* (2016.08); *A23V 2002/00* (2013.01); *A23V 2200/326* (2013.01); *A23V 2200/328* (2013.01); *A23V 2200/3262* (2013.01); *A23V 2250/7052* (2013.01)

(58) Field of Classification Search
CPC ................ A61K 31/4415; A61K 45/06; A23V 2200/36; A23V 2200/3262; A23V 2200/328; A23V 2250/7052; A23V 2200/326; A23V 2200/332; A23L 33/15; A23L 33/30; A23L 33/40; A61P 3/00; A61P 3/04; A61P 3/08; A61P 3/10
See application file for complete search history.

(56) References Cited

U.S. PATENT DOCUMENTS

| 6,258,846 B1* | 7/2001 | Hermelin ................ A23L 33/10 424/439 |
|---|---|---|
| 2004/0230257 A1* | 11/2004 | Ovokaitys ............ A61K 31/198 607/88 |
| 2008/0187606 A1 | 8/2008 | Kim et al. |
| 2010/0092610 A1 | 4/2010 | Haschke |
| 2010/0111915 A1 | 5/2010 | Isolauri et al. |
| 2012/0027897 A1 | 2/2012 | Innocenzi |

FOREIGN PATENT DOCUMENTS

| CN | 1032953 A | 10/1994 | |
|---|---|---|---|
| CN | 103478261 A | 1/2014 | |
| EP | 1499285 A2 | 1/2005 | |
| EP | 2147678 | 1/2010 | |
| WO | 2007135141 | 11/2007 | |
| WO | 2007135141 A1 | 11/2007 | |
| WO | WO-2011150393 A2 * | 12/2011 | ................ A61P 7/02 |

OTHER PUBLICATIONS

Yates et. al., Journal of the American Dietetic Association, 1998, vol. 98, pp. 699-706 (Year: 1998).*
Butte et. al., Public Health Nutrition, 2005, vol. 8(7A), pp. 1010-1027 (Year: 2005).*
Schuster et. al., Journal of Nutrition, 1984, American Institute for Nutrition, vol. 114(5), pp. 977-988 (Year: 1984).*
Borschel et. al., The American Journal of Clinical Nutrition, 1986, American Society for Clinical Nutrition, vol. 43, pp. 7-15 (Year: 1986).*
McCarty "Prenatal high-dose pyridoxine may prevent hypertension and syndrome X in-utero by protecting the fetus from excess glucocorticoid activity" Medical Hypotheses, 2000, vol. 54, No. 5, pp. 808-813.
Dror et al. "Interventions with Vitamins B6, B12 and C in Pregnancy" Paediatric and Perinatal Epidemiology, 2012, vol. 26, suppl. 1, pp. 55-74.

(Continued)

*Primary Examiner* — Sarah Pihonak
(74) *Attorney, Agent, or Firm* — K&L Gates LLP

(57) ABSTRACT

The present invention generally relates to the early prevention of overweight, obesity, excessive fat accumulation and/or associated metabolic disorders in infants or children. For example, the present invention relates to the prevention of overweight, obesity, excessive fat accumulation and/or associated metabolic disorders in infants or children through appropriate nutrition for women desiring to get pregnant and/or during pregnancy and/or lactation. Embodiments of the present invention relate to the Vitamin B6 for use in the prevention of overweight, obesity, excessive fat accumulation and/or associated metabolic disorders in the offspring, wherein the vitamin B6 is administered to women desiring to get pregnant and/or to the mother during pregnancy and/or lactation and to maternal food compositions that can be used for this purpose.

14 Claims, 2 Drawing Sheets

(56) References Cited

OTHER PUBLICATIONS

Yajnik et al. "Vitamin B12 and folate concentrations during pregnancy and insulin resistance in the offspring: the Pune Maternal Nutrition Study" Diabetologia, 2008, vol. 51, pp. 29-38.
Ciappio et al. "Maternal one-carbon nutrient intake and cancer risk in offspring" Nutrition Reviews, 2011, vol. 69, No. 10, pp. 561-571.
Crozier et al. "Maternal vitamin D status in pregnancy is associated with adiposity in the offspring: findings from the Southampton Women's Survey1-4" Am J Clin Nutr, 2012, vol. 96, pp. 57-63.
Kipping et al. British Medical Journal, 2008, British Medical Association, vol. 337, pp. 922-927.

* cited by examiner

MATERNAL VITAMIN B6 ADMINISTRATION FOR THE PREVENTION OF INCREASED ADIPOSITY, OVERWEIGHT OR OBESITY IN THE OFFSPRING

PRIORITY CLAIM

This application is a continuation of U.S. application Ser. No. 15/109,713 filed Jul. 5, 2016, which is a National Stage of International Application No. PCT/EP2015/050358 filed Jan. 9, 2015, which claims priority to European Patent Application No. 14150798.8 filed Jan. 10, 2014, and European Patent Application No. 14161188.9 filed Mar. 21, 2014, the entire contents of which are incorporated herein by reference.

FIELD OF THE INVENTION

The present invention generally relates to the early prevention of overweight, obesity, excessive fat accumulation and/or associated metabolic disorders in infants or children. For example, the present invention relates to the prevention of overweight, obesity, excessive fat accumulation and/or associated metabolic disorders in infants or children through appropriate maternal nutrition before pregnancy, during pregnancy and/or during lactation. Embodiments of the present invention relate to vitamin B6 for use in the prevention of overweight, obesity, excessive fat accumulation and/or associated metabolic disorders in the offspring, wherein the vitamin B6 is administered to the mother before pregnancy, during pregnancy and/or during lactation and to maternal food compositions that can be used for this purpose.

BACKGROUND

Scientific evidence has accumulated showing that prenatal and post natal early nutrition and other environmental factors cause programming of long-term health and well-being, and can impact the risk of developing chronic diseases. Several studies have shown that changes in dietary intake or manipulation of individual macro and micronutrients during the reproductive period can have an impact in several physiological processes, such as growth, metabolism, appetite, cardiovascular function among others (Koletzko B et al (2011) Am J Nutr 94(s):2036-435). Therefore nutritional status (nutrient stores and dietary intake) of women before and during pregnancy is of relevance to optimize neonatal and child health outcomes. Maternal nutrition is thought to affect the availability and supply of nutrients to the developing fetus that are required for critical developmental processes.

Childhood overweight and obesity are major public health problem in a wide range of countries (including middle and low-income countries) and increasing rates of overweight and obesity have been reported in the last three decades. In 2008 in the UK about 30% of children 2-15 years old were overweight or obese. Evidence shows that weight at 5 years of age is good indicator of future health and well-being of a child (Gardner et al (2009) Pediatrics 123:e67-73). It has been shown that obesity in childhood increases the risk of adult obesity and other highly detrimental chronic conditions such as, cardiovascular disease, type 2 diabetes, hepatic, renal and musculoskeletal complications, etc, among others. There is strong evidence that once obesity is established it is difficult to reverse through interventions and continues till adulthood (Waters E et al. (2011) Cochrane Database of Systematic Reviews 12), underlining the importance of childhood obesity prevention efforts.

Some possible early-life determinants including maternal obesity and diabetes, excess gestational weight gain, maternal smoking, rapid infant growth have been clearly associated with later in life overweight and obesity (Monasta L et al. (2010) Obesity Reviews. 11:695-708). Although the association may be modest for each of these factors, a large effect may be achieved when acting on a small attributable risk if the risk factor is highly prevalent in a population. Also some possible determinants may become more important than others because they are easier to be addressed through the implementation of an effective intervention.

Micronutrient deficiencies have profound and often persistent effects on fetal tissues and organs, even in the absence of clinical signs of their deficiency in the mother (Ashworth C J et al (2001) 122:527-35). Inadequate intakes of multiple micronutrients are common among women of reproductive age living in resource poor-settings (Torhem L E et al. (2010) J. Nutr. 140: 2051S-58S), and in some settings malnourishment related to overweight and obesity are also emerging concerns due to poor diet.

The inventors have investigated micronutrient deficiencies in women in order to identify micronutrients that can be used in prenatal and post natal early nutrition to program long-term health and well-being, and that—in particular—have a positive impact on reducing the risk of developing chronic diseases, such as overweight, obesity and associated metabolic disorders such as diabetes, cardiovascular diseases and hypertension.

Any reference to prior art documents in this specification is not to be considered an admission that such prior art is widely known or forms part of the common general knowledge in the field.

It would therefore be desirable to provide the art with a solution that allows it to reduce the likelihood of developing overweight, obesity, excessive fat accumulation and/or associated disorders as early in life as possible.

One object of the present invention is to improve the state of the art and in particular to provide a solution that overcomes at least some of the disadvantages of the present state of the art and that satisfies the needs expressed above, or to at least provide a useful alternative.

SUMMARY

The invention relates to the use of Vitamin B6 for use in the prevention of overweight, obesity, excessive fat accumulation and/or associated metabolic disorders in the offspring. The vitamin B6 is to be administered to women desiring to get pregnant and/or to the mother during pregnancy and/or lactation, in various forms.

DESCRIPTION OF THE INVENTION

The present inventors were surprised to see that they could achieve the above objectives by the subject matter of the independent claims. The dependent claims further develop the idea of the present invention.

The present inventors have investigated the role of epigenetics as a mediator and a marker of early nutritional effects on human childhood body composition and the risk of humans developing obesity and insulin-resistance related disorders later in life. They have conducted thorough and detailed analyses in multi-cohort studies and were surprised to find that a vitamin B6 deficiency in expecting mothers led to an increased likelihood that their offspring develops overweight, obesity, excessive fat accumulation and/or associated metabolic disorders.

Consequently, the present invention relates in part to vitamin B6 for use in the prevention of overweight, obesity, excessive fat accumulation and/or associated metabolic disorders in the offspring.

The present invention also relates to the use of vitamin B6 for the preparation of a composition for the prevention of overweight, obesity, excessive fat accumulation and/or associated metabolic disorders in the offspring. The use may be non-therapeutic use.

The present invention further relates to vitamin B6 for use in the reduction of the likelihood for the development of overweight, obesity, excessive fat accumulation and/or associated metabolic disorders in the offspring.

Alternatively, according to any embodiment of the invention as described herein, vitamin B6 or a composition comprising vitamin B6 is used to prevent or to reduce the likelihood for the development of overweight, obesity, associated metabolic disorders and/or excessive fat accumulation.

The vitamin B6 may be for example to be administered to the mother before pregnancy, during pregnancy and/or during lactation.

Vitamin B6 supplementation is in particular effective in mothers which have low levels of vitamin B6 and/or have insufficient vitamin B6 intake.

Vitamin B6 intake is considered insufficient if it is below the Recommended Dietary Allowance (RDA). The RDA is the daily dietary intake level of a nutrient considered sufficient to meet the requirements of 97.5% of healthy individuals in each life-stage and gender group. It is calculated based on the Estimated Average Requirements (EAR), which are expected to satisfy the needs of 50% of the people in that age group based on a review of the scientific literature.

For example, the Vitamin B6 intake of a pregnant woman may be considered insufficient if it is below 1.9 mg/day.

Presently, vitamin B6 supplementation is used in the art during pregnancy to treat or prevent nausea and/or vomiting.

"Overweight" is defined for an adult human as having a BMI between 25 and 30.

"Body mass index" or "BMI" means the ratio of weight in kg divided by the height in meters, squared.

"Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

For children the BMI is plotted on a BMI vs. age growth chart (for either girls or boys) to obtain a percentile ranking. Percentiles are the most commonly used indicator to assess the size and growth patterns of individual children. The percentile indicates the relative position of the child's BMI among children of the same sex and age. Children are considered overweight if their BMI is located between the 85" and 95" percentile. Children are considered obese if their BMI is located on or above the 95" percentile.

Metabolic disorders that are associated with overweight, obesity and/or excessive fat accumulation are similar and well known to skilled artisans. For example, these disorders include cardiovascular diseases such as coronary heart disease; insulin resistance; type 2 diabetes; hypertension; sleep apnea, respiratory problems and/or dyslipidemia; but also some cancers such as endometrial, breast, and/or colon cancer; stroke; liver and gallbladder disease; osteoarthritis; and/or gynecological problems.

As vitamin B6 may be administered to expecting mothers during pregnancy and/or to mothers during lactation it may for example be administered in the form of a maternal food composition.

Women's nutrient needs increase during pregnancy and lactation. If the increased nutrient needs are satisfied this protects maternal and infant health. Lactation is demanding on maternal stores of energy, protein, and other nutrients that need to be established, and replenished.

Maternal food compositions are food compositions designed to help meeting the specific nutritional requirements of women during pregnancy and lactation.

For example, such maternal food compositions may comprise sources of protein, iron, iodine, vitamin A, and/or folate.

The maternal food composition may have any form that is accepted by mothers as part of their diet or as nutritional supplement.

For example, the maternal food composition may be selected from the group consisting of a powdered nutritional composition to be reconstituted in milk or water, a nutritional formula, a cereal based-product, a drink, a bar, a nutritional supplement, a nutraceutical, a yogurt a milk-derived product, a food sprinkler, a pill or a tablet.

Currently, particularly well accepted by consumers are powdered nutritional compositions to be reconstituted in milk or water.

Also well accepted are nutritional supplements, for example in the form of a tablet. The supplement provides selected nutrients while not representing a significant portion of the overall nutritional needs of the subject and/or does not represent more than 0.1%, 1%, 5%, 10%, or 20% of the daily energy need of the subject Vitamin B6 may be used in any amount that is effective in achieving the objective of the present invention. Skilled artisans will be able to determine appropriate dosages. Typically, dosage will depend on age, size and health status of the mother, on her lifestyle as well as on her genetic heritage.

In the prophylactic applications of the present invention, Vitamin B6 is administered in an amount that is sufficient to at least partially reduce the risk of the development of overweight, obesity, excessive fat accumulation and/or associated metabolic disorders in the offspring. Such an amount is defined to be "a prophylactic effective dose". Hence, vitamin B6 may be administered in a prophylactic effective dose.

For example, the vitamin B6 is administered in an amount corresponding to 0.19-60 mg Vitamin B6/day, for example 1-40.0 mg Vitamin B6/day.

For the purpose of the present invention it is preferred if Vitamin B6 is administered regularly, for example two times a day, daily, every two days, or weekly.

The vitamin B6 may be provided as a sustained release formulation. This way, vitamin B6 can be consumed less frequently, while the body is still constantly supplied with sufficient Vitamin B6.

For example the vitamin B6 may be administered before pregnancy (pre-pregnancy), during the part of or the whole pregnancy and/or during the breastfeeding period (lactation). In one embodiment vitamin B6 may be administered during pregnancy and/or during lactation.

In one embodiment the composition of the invention is administered before pregnancy, for example during the 1, 2, or 4 months preceding the pregnancy or desired pregnancy.

As the nutritional requirements increase in the second and particularly the third trimester of pregnancy, it may be preferred to administer Vitamin B6 regularly throughout the third trimester of pregnancy or throughout the second and third trimester of pregnancy.

For example, vitamin B6 may be to be administered daily. The regular administration of vitamin B6 may be continued for at least at least 4, at least 8, at least 12, at least 16, at least 20, at least 24, at least 28, at least 32, or at least 36 consecutive weeks during pregnancy and/or during lactation.

Vitamin B6 may be used in pure form or as a natural vitamin B6 source or an extract thereof.

Highly purified or synthetic vitamin B6 may be used. It is preferred if vitamin B6 is provided from natural sources or as a natural source.

For example, vitamin B6 may be provided from natural sources such as fish; organ meats, such as beef liver; meats; eggs; crude rice and wheat; potatoes; vegetables rich in starch, such as chickpeas, peas, beans, squash; fruit; dried herbs and spices; nuts such as pistachios and hazelnuts; seeds, such from sunflower or sesame or extracts and/or combinations thereof.

Vitamin B6 may be used as single active ingredient.

It may also be co-administered with one or more other compounds that are active in reducing the risk of developing overweight, obesity, excessive fat accumulation and/or associated metabolic disorders in the offspring if administered to the mother before pregnancy, during pregnancy and/or during lactation.

Vitamin B6 may for example be administered in combination with vitamin D for example vitamin D3.

The administration of vitamin B6 in combination with vitamin D may be particularly beneficial because it may lead to an improved effect in comparison to when vitamin B6 or vitamin D is administered alone.

In accordance with the present invention, vitamin B6 may be used to prevent the generation of overweight, obesity, excessive fat accumulation and/or associated metabolic disorders in the offspring later in life.

"Later in life" includes childhood and adulthood. For example, "later in life" may refer to childhood, such as to an age of at least 3 years, for example at least 4 years or at least 6 years.

The inventors have found that the subject matter of the present invention allows it in particular to prevent overweight and/or obesity by reducing and/or avoiding the excessive build-up of body fat mass in the offspring, for example abdominal and/or visceral fat mass.

This is advantageous as abdominal fat is particularly strongly correlated with cardiovascular diseases as well as other metabolic and vascular diseases, such as type 2 diabetes. Visceral fat, also known as intra-abdominal fat, is located inside the peritoneal cavity, between internal organs and torso and is also strongly correlated with type 2 diabetes.

It may further be preferred to administer vitamin B6 in accordance with the present invention to mothers and/or expecting mothers whose children are particularly at risk of developing of overweight, obesity, excessive fat accumulation and/or associated metabolic disorders.

The studies leading to the present invention have shown that these may be for example multiparous, overweight and/or obese mothers and/or mothers suffering from metabolic syndrome.

The present invention also relates to a maternal food composition that can be used for the purpose of the present invention.

Consequently, the present invention relates to a maternal food composition, wherein the maternal food composition is a powdered nutritional formula comprising a protein source, a carbohydrate source, a lipid source, lecithin such as soya lecithin, a bulking agent and 0.27-27 mg vitamin B6/100 g dry weight.

The protein source may be dried milk or dried skimmed milk. As carbohydrate source sucrose and/or maltodextrin may be used. The lipid source may be vegetable oil. Vitamins and minerals may be also be added. For example, vitamins and minerals may be added in accordance with the recommendations of Government bodies such as the USRDA. For example, the composition may contain per daily dose one or more of the following micronutrients in the ranges given: 100 to 2500 mg calcium, 35 to 350 mg magnesium, 70 to 3500 mg phosphorus, 2.7 to 45 mg iron, 1.1 to 40 mg zinc, 0.1 to 10 mg copper, 22 to 1,100 μg iodine, 6 to 400 μg selenium, 77 to 3000 μg of vitamin A or retinol activity equivalents (RAE), 8.5 to 850 mg Vitamin C, 0.14 to 14 mg Vitamin B1, 0.14 to 14 mg Vitamin B2, 1.8 to 35 mg niacin, 0.26 to 26 μg Vitamin B12, 60 to 1000 μg folic acid, 3 to 300 μg biotin, 1.5 to 100 μg Vitamin D, 1.9 to 109 μg Vitamin E.

The formulation may also alternatively or additionally contain glucose syrup, milk fat, fish oil, magnesium citrate, choline salts and esters, probiotic cultures, prebiotic fibers, and/or ascorbyl palmitate.

Flavor compounds, such as cocoa powder or honey, for example, may be added to provide taste variations.

The composition may further contain probiotic bacteria, folic acid, calcium, iron, ARA, EPA, and/or DHA.

Those skilled in the art will understand that they can freely combine all features of the present invention described herein, without departing from the scope of the invention as disclosed. In particular, features described for the uses of the present invention may be applied to the maternal food composition of the present invention and vice versa.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification. Further advantages and features of the present invention are apparent from the figures and non-limiting examples.

BRIEF DESCRIPTION OF THE FIGURES AND DRAWINGS

EXAMPLES

Figure 1:
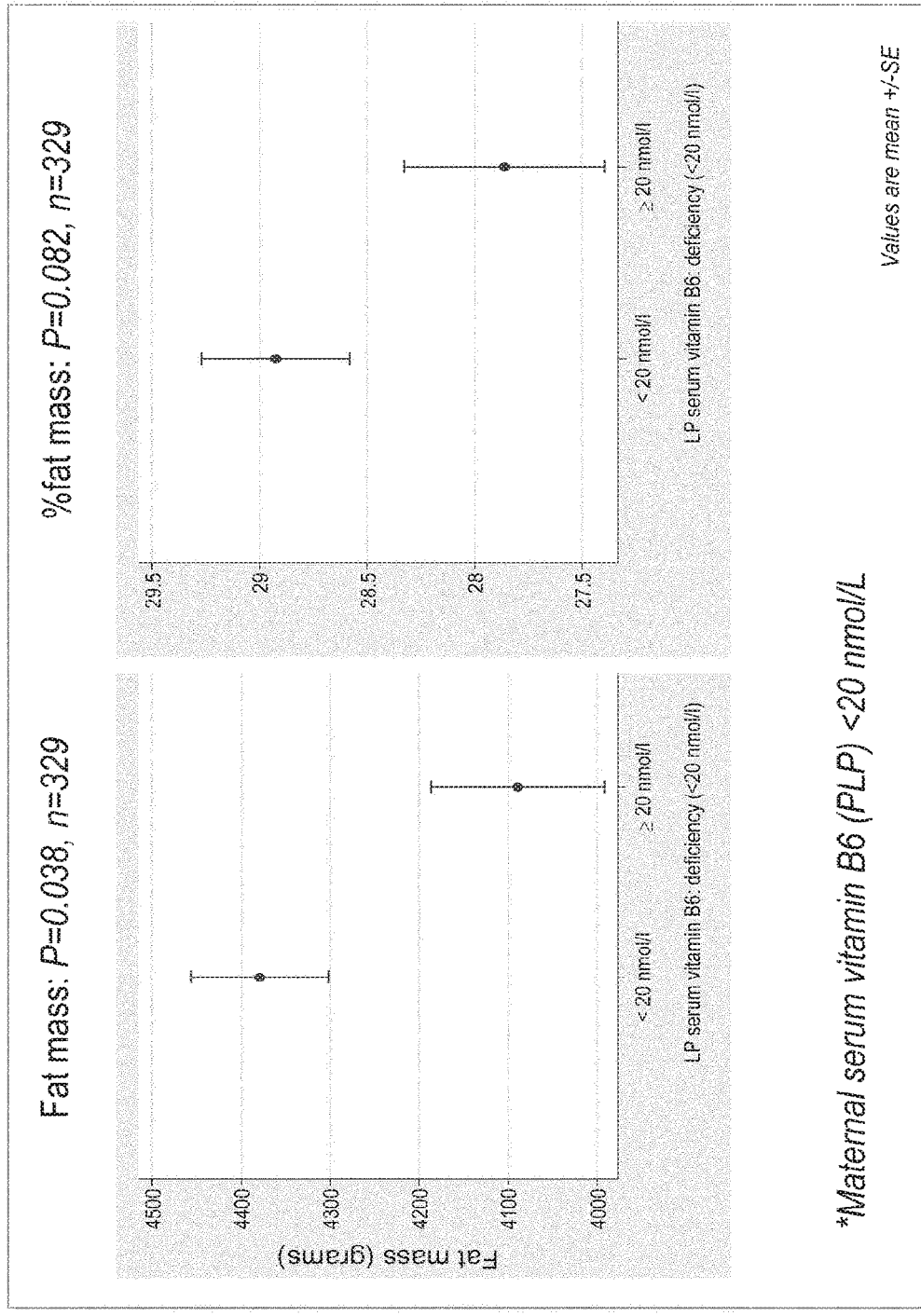
FIG. 1 shows that women presenting vitamin B6 deficiency (serum levels <20 nmol) in late pregnancy deliver offspring with greater child's adiposity measured by dual X-ray absorptiometry (DXA) at age 4 years. In panel a) higher fat mass values (grams) in the offspring were significantly associated to the maternal vitamin B6 deficiency and in b) a trend was observed for the % of fat mass.

Experimental and clinical research suggests that maternal nutritional state during pregnancy has lifelong effects in later in life outcomes in the offspring. In our work we seek to identify clinically and nutritionally defined groups whose offspring are at increased risk of later suboptimal body composition.

Study Design:

Mother-infant cohort included in the analysis:

501 Southampton Women's Survey (SWS) mother-infant pairs were selected as those with a late pregnancy maternal serum aliquot together with DXA measurements of body composition of the offspring at age 4 and 6 years. Summary characteristics of the SWS subjects analyzed were the following:

|  | Number | Percentage |
| --- | --- | --- |
| Parity | | |
| Primiparous | 244 | 48.7% |
| Multiparous | 257 | 51.3% |
| Maternal Age (years) | | |
| <25 | 34 | 6.8% |
| 25-35 | 398 | 79.4% |
| ≥35 | 69 | 13.8% |
| Ethnicity | | |
| White Caucasian | 486 | 97.0% |
| Non-white Caucasian | 15 | 3.0% |
| Maternal Pre-pregnant BMI | | |
| <20 kg/m2 | 32 | 6.5% |
| ≥20 kg/m2 | 464 | 93.5% |

1) Measurements of Vitamin B6 (PLP) in Maternal Serum Samples.

A reverse-phase high performance liquid chromatography (HPLC) method with post column derivatisation and fluorimetric detection was used to determine pyridoxal -5¬phosphate (PLP). [Rybak M E, Pfeiffer C M. Clinical analysis of vitamin B6: Determination of pyridoxal 50-phosphate and 4-pyridoxic acid in human serum by reversed-phase high-performance liquid chromatography with chlorite post column derivatization. Analytical Biochemistry 2004; 333:336-344.] QC was achieved through internal procedures as there were no external quality schemes for the vitamin B6 HPLC method. QC material was produced by spiking human plasma with aqueous solutions of PLP. The final QC concentration was designed to match typical mid-range human samples and previously provided CDC 'mid bench' quality controls. The QC material was spiked so that the additional aqueous content represented only 0.02% of the total medium. Duplicate analysis of the QC material was performed with each analytical run. When the mean percentage recovery was outside of the range 95 to 105% of nominal the analytical results for that run were corrected accordingly. Good agreement between the obtained values for PLP in the quality control and the expected values indicates a high degree of accuracy for this method.

For a few of the samples repeated analysis was undertaken where the initial analysis yielded concentration values outside of the calibration ranges. An even smaller number had concentrations reported as less than the lowest calibration standard because, for the most part, it was not possible to re analyse these samples. This approach means that some re-analysed samples are reported as concentration values much lower than the bottom standard while a few are represented as less than values. For statistical analysis we have assigned a value midway between 0 and the bottom of the calibration range to those (3 subjects) with values less than the bottom standard. One subject had no PLP peak, so their PLP concentration was set as "0".

Vitamin B6 status is usually assessed by plasma PLP levels. Exported from liver as a PLP-albumin complex, plasma PLP is considered a reflection of hepatic B6 levels and stores [Lumeng L, Ryan M P, Li T K. Validation of the diagnostic value of plasma pyridoxal 50-phosphate measurements in vitamin B6 nutrition of the rat. J Nutr 1978; 108:545-553; Li A, Lumeng L, Aronoff G R, Li T-K. Relationship between body store of vitamin B6 and plasma pyridoxal-P clearance: metabolic balance studies in humans. J Lab Clin Med 1985; 106:491-497.]. Although some support a threshold of 30 nmol/l [Leklem J E. Vitamin B-6: a status report. J Nutr 1990; 120:1503-1507.], plasma PLP levels of <20 nmol/l are considered to reflect adverse vitamin status in the adult [Coburn S P, Lewis D L, Fink W J, Mahuren J D, Schaltenbrand W E, Costill D L. Human vitamin B6 pools estimated through muscle biopsies. Am J Clin Nutr 1988; 48:291-294.] for assessing sufficiency. Plasma levels of other B6 vitamers are sometimes measured, but these tend to fluctuate more than PLP levels and are influenced by recent dietary intake [Contractor S F, Shane B. Estimation of vitamin B6 compounds in human blood and urine. Clin Chim Acta 1968; 21:71-77].

For initial SWS analyses a level of serum PLP <20 nmol/L was used to indicate deficient B6 status, 2) Statistical Analyses to Uncover the Associations of the Deficiencies to Childhood Adiposity in SWS.

All SWS children's fat mass variables were positively skewed and were transformed with the use of Fisher-Yates normal scores to a normally distributed variable with a mean of 0 and an SD of 1 [Armitage P, Berry G. Statistical methods in medical research. Oxford, United Kingdom: Blackwell Science Ltd, 2002.]. Linear regression models were fitted with body-composition variables as the outcomes and with maternal micronutrient status as the predictor, taking account of potential confounding influences. Owing to sex differences in the children's body composition, all analyses were adjusted for the sex of the child, together with the child's age. Statistical analysis was performed with the use of Stata 11.1 [StataCorp. Stata: release 11. Statistical software. College Station, Tex.: StataCorp LP, 2009.] Thresholds for the statistical analysis of micronutrient deficiency/insufficiency are described in the text above.

Results:

The results of PLP and PA in serum samples indicate that vitamin B6 deficiency is extremely prevalent in late gestation pregnant women in Southampton, a total of 70.0% of the 501 subjects had serum PLP levels <20 nmol/L.

Maternal vitamin B6 deficiency in late pregnancy was both associated with greater offspring fat mass measured by DXA at 4 and 6 years.

TABLE 1

Child's adiposity by maternal vitamin B6 status.

| DXA results | | Vitamin B6 levels | | |
| --- | --- | --- | --- | --- |
| Age at Measurement | Fat content | <20 nmol/L | ≥20 nmol/L | P-value |
| 4 years old | Total (ln g) (log-transformed) | 8.35 (231) | 8.29 (98) | 0.038 |
|  | Percentage | 28.9 (231) | 27.9 (98) | 0.082 |

TABLE 1-continued

Child's adiposity by maternal vitamin B6 status.

DXA results

| Age at Measurement | Fat content | Vitamin B6 levels | | P-value |
|---|---|---|---|---|
| | | <20 nmol/L | ≥20 nmol/L | |
| 6 years old | Total (ln g) (log-transformed) | 8.54 (342) | 8.47 (142) | 0.035 |
| | Percentage (In) (log-transformed) | 3.25 (341) | 3.19 (141) | 0.012 |

Figure 2:
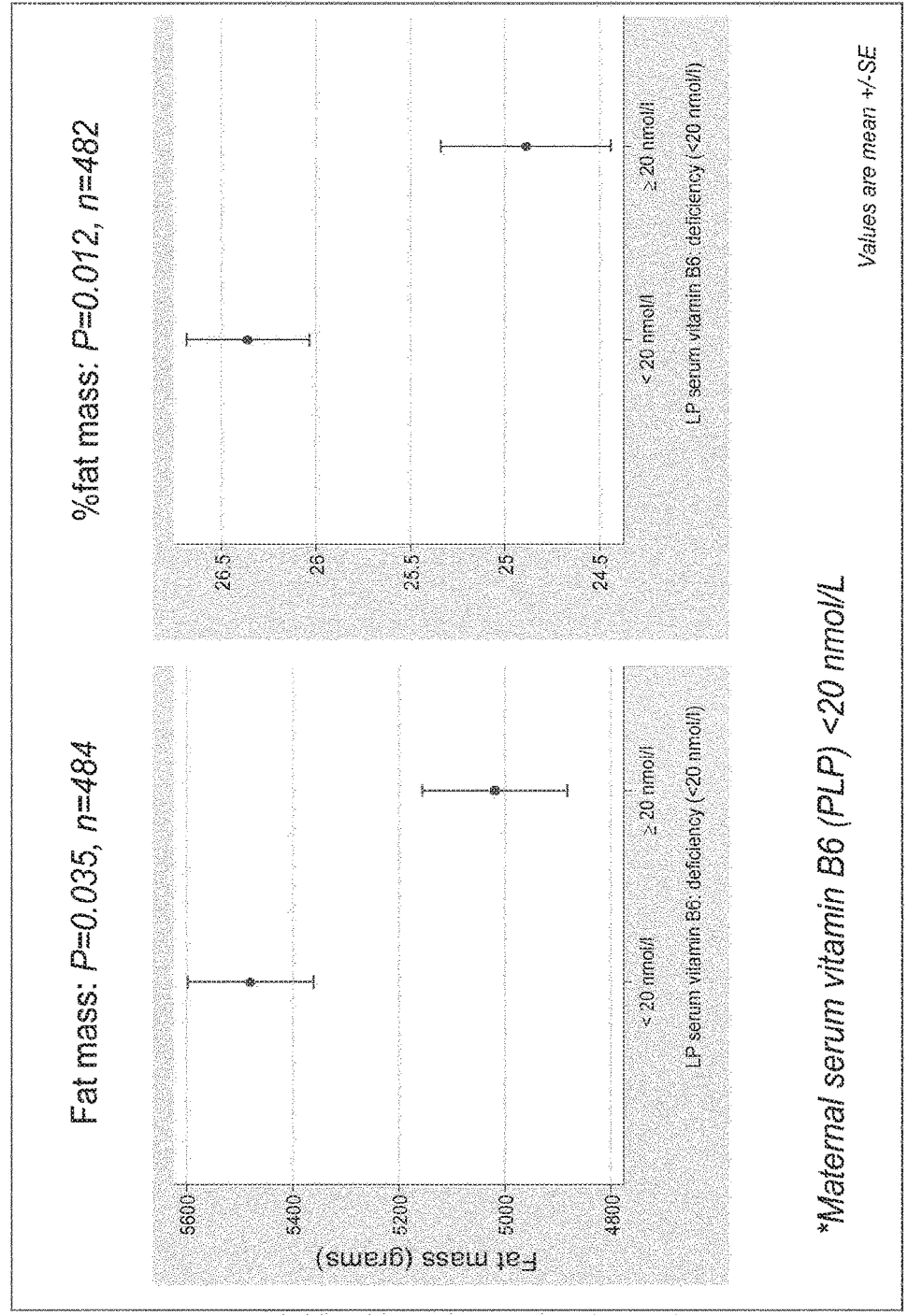
FIG. 2 shows that women presenting vitamin B6 deficiency (serum levels <20 nmol) in late pregnancy deliver offspring with greater child's adiposity measured by DXA at age 6 years. In panel a) higher fat mass values (grams) and in b) the % of fat mass in the offspring were significantly associated to the maternal vitamin B6 deficiency.

The results shown in the table 1 correspond to the log-transformed values used for the statistical analysis of the measures plotted in FIGS. 1 and 2. Fat content percentage at 4 years distribution was not skewed so it was not log-transformed.

Mean serum levels of Vitamin B6 showed significant differences according to parity and pre-pregnancy BMI (Table 2) and multiparous and obese mothers were identified at higher risk of maternal vitamin B6 deficiency (Table 3),

TABLE 2

Vitamin B6 status according to parity and pre-pregnancy BMI.

| | Mean serum vitamin B6 (PLP) (nmol/L) |
|---|---|
| Parity | |
| Primiparous | 16.8 |
| Multiparous | 13.5 |
| p-value (from t-test) | <0.001*** |
| Pre-pregnant BMI | |
| <18.5 | 9.8 |
| 18.5-25 | 16.2 |
| 25-30 | 14.2 |
| >30 | 12.5 |
| p-value (from ANOVA) | 0.01* |

TABLE 3

Increased risk of vitamin B6 deficiency according to parity and pre-pregnancy BMI.

| | Odds ratio | 95% CI | P value |
|---|---|---|---|
| Parity | | | |
| Primiparous | Referent | | |
| Multiparous | 2.08 | 1.41, 3.07 | <0.001*** |
| Pre-pregnant BMI | | | |
| 18.5-25 | Referent | | |
| 25-30 | 1.90 | | 0.006** |
| >30 | 2.13 | 1.11, 4.10 | 0.024* |

These results support that vitamin B6 deficiency has lasting effects on the offspring's risk of obesity and provide strong support for intervening before pregnancy, during pregnancy and during lactation to improve maternal vitamin B6 status.

The invention is claimed as follows:

1. A method of reducing the likelihood of developing overweight and/or excessive build-up of abdominal and/or visceral fat mass in adulthood of an offspring of a mother having a vitamin B6 intake of below 1.9 mg/day or having a vitamin B6 serum level of less than 20 nmol/l, the method comprising administering a composition in a daily dose comprising Vitamin B6 in an amount of 2.5-60 mg Vitamin B6/day to the mother at a time period selected from the group consisting of before pregnancy, during pregnancy, during lactation, and combinations thereof, wherein the composition further comprises a component selected from the group consisting of probiotic bacteria, folic acid, calcium, iron, arachidonic acid (ARA), eicosapentaenoic acid (EPA), docosahexaenoic acid (DHA), and mixtures thereof.

2. The method of claim 1, wherein the composition is in the form of a maternal food composition.

3. The method in accordance with claim 2, wherein the maternal food composition is selected from the group consisting of a powdered nutritional composition to be reconstituted in milk or water, a nutritional formula, a cereal based-product, a drink, a bar, a nutritional supplement, a nutraceutical, a yogurt, a milk-derived product, a food sprinkler, a pill and a tablet.

4. The method of claim 1, wherein the composition is administered to the mother for at least 4 consecutive weeks before pregnancy, during pregnancy, and/or during lactation.

5. A method of reducing the likelihood of developing overweight and/or excessive build-up of abdominal and/or visceral fat mass in adulthood of an offspring of a mother having a vitamin B6 intake of below 1.9 mg/day or having a vitamin B6 serum level of less than 20 nmol/l, the method comprising administering a composition in a daily dose comprising Vitamin B6 in an amount of 2.5-60 mg Vitamin B6/day to the mother at a time period selected from the group consisting of before pregnancy, during pregnancy, during lactation, and combinations thereof, wherein the composition is provided from a source selected from the group consisting of fish, meat, egg, crude rice, crude wheat, potatoes, chickpeas, peas, beans, squash, fruit, dried herbs, dried spices, nuts, seeds, extracts thereof, and combinations thereof.

6. A method of reducing the likelihood of developing overweight and/or excessive build-up of abdominal and/or visceral fat mass in adulthood of an offspring of a mother having a vitamin B6 intake of below 1.9 mg/day or having a vitamin B6 serum level of less than 20 nmol/l, the method comprising administering a composition in a daily dose comprising Vitamin B6 in an amount of 2.5-60 mg Vitamin B6/day to the mother at a time period selected from the group consisting of before pregnancy, during pregnancy, during lactation, and combinations thereof, wherein the mother is a multiparous, overweight and/or obese mother and/or a mother suffering from metabolic syndrome.

7. A method of reducing the likelihood of developing overweight and/or excessive build-up of abdominal and/or visceral fat mass in adulthood of an offspring of a mother having a vitamin B6 intake of below 1.9 mg/day or having a vitamin B6 serum level of less than 20 nmol/l, the method comprising administering a composition in a daily dose comprising Vitamin B6 in an amount of 2.5-60 mg Vitamin B6/day to the mother at a time period selected from the group consisting of before pregnancy, during pregnancy, during lactation, and combinations thereof, wherein the composition further comprises a component selected from the group consisting of a protein source, a carbohydrate source, a lipid source, lecithin, bulking agents, and mixtures thereof.

8. The method of claim 1, wherein the composition is administered in a daily dose comprising vitamin B6 in an amount of 2.5-40 mg Vitamin B6/day.

9. The method of claim 1, wherein the composition is administered in a frequency selected from the group consisting of two times a day, daily, every two days, weekly, and combinations thereof.

10. A method of reducing the likelihood of developing overweight and/or excessive build-up of abdominal and/or visceral fat mass in adulthood of an offspring of a mother having a vitamin B6 intake of below 1.9 mg/day or having a vitamin B6 serum level of less than 20 nmol/l, the method comprising administering a composition in a daily dose comprising Vitamin B6 in an amount of 2.5-60 mg Vitamin B6/day wherein the composition is administered to the mother daily for at least 36 consecutive weeks during pregnancy and/or during lactation.

11. The method of claim 1, wherein the composition is administered in a daily dose comprising Vitamin B6 in an amount of 2.6-40 mg Vitamin B6/day.

12. A method of reducing the likelihood of developing overweight and/or excessive build-up of abdominal and/or visceral fat mass in adulthood of an offspring of a mother having a vitamin B6 intake of below 1.9 mg/day or having a vitamin B6 serum level of less than 20 nmol/l, the method comprising administering a composition in a daily dose comprising Vitamin B6 in an amount of 2.5-60 mg Vitamin B6/day to the mother before pregnancy.

13. The method of claim 12, wherein the composition is administered to the mother during one, two, or four months preceding the pregnancy.

14. A method of reducing the likelihood of developing overweight and/or excessive build-up of abdominal and/or visceral fat mass in adulthood of an offspring of a mother having a vitamin B6 intake of below 1.9 mg/day or having a vitamin B6 serum level of less than 20 nmol/l, the method comprising administering a composition in a daily dose comprising Vitamin B6 in an amount of 2.5-60 mg Vitamin B6/day to the mother at a time period selected from the group consisting of before pregnancy, during pregnancy, during lactation, and combinations thereof, wherein the Vitamin B6 is provided as a sustained release formulation.

* * * * *